(12) United States Patent
Kaur et al.

(10) Patent No.: US 8,318,217 B2
(45) Date of Patent: Nov. 27, 2012

(54) COMPOSITIONS COMPRISING AN ANTI-INFLAMMATORY BLEND

(75) Inventors: Simarna Kaur, Green Brook, NJ (US); Michael Southall, Lawrenceville, NJ (US); Samantha D. Tucker-Samaras, Long Valley, NJ (US); Claude Saliou, Basking Ridge, NJ (US); Khalid Mahmood, South Hadley, MA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 23 days.

(21) Appl. No.: 12/896,250

(22) Filed: Oct. 1, 2010

(65) Prior Publication Data

US 2011/0081433 A1 Apr. 7, 2011

Related U.S. Application Data

(60) Provisional application No. 61/247,992, filed on Oct. 2, 2009.

(51) Int. Cl.
*A61K 36/00* (2006.01)
*A61K 36/756* (2006.01)
*A61K 36/28* (2006.01)
*A61K 36/16* (2006.01)
*A61K 36/815* (2006.01)
*A61K 36/21* (2006.01)
*A61K 36/8967* (2006.01)
*A61K 36/63* (2006.01)

(52) U.S. Cl. .................. 424/725; 424/764; 424/752
(58) Field of Classification Search .................. None
See application file for complete search history.

(56) References Cited

U.S. PATENT DOCUMENTS

| | | | |
|---|---|---|---|
| 1,649,670 A | 11/1927 | Dohme et al. | |
| 3,193,507 A | 7/1965 | Jacobs | |
| 4,093,667 A | 6/1978 | Starks | |
| 4,337,370 A | 6/1982 | Takisawa et al. | |
| 4,959,393 A | 9/1990 | Torihara et al. | |
| 5,705,145 A | 1/1998 | Miklean et al. | |
| 6,852,310 B2 | 2/2005 | Harichian et al. | |
| 6,863,897 B2 | 3/2005 | Love et al. | |
| 6,869,598 B2 | 3/2005 | Love et al. | |
| 7,468,464 B2 | 12/2008 | Harichian et al. | |
| 8,084,504 B2 | 12/2011 | Johnson et al. | |
| 2004/0109832 A1 | 6/2004 | Harichian et al. | |
| 2005/0048008 A1* | 3/2005 | Gupta | 424/59 |
| 2006/0019002 A1 | 1/2006 | Xue | |
| 2006/0120975 A1 | 6/2006 | Scheri et al. | |
| 2006/0210497 A1 | 9/2006 | Harichian et al. | |
| 2006/0264497 A1 | 11/2006 | Zeligs | |
| 2006/0269504 A1 | 11/2006 | James | |
| 2006/0292184 A1 | 12/2006 | Richardson et al. | |
| 2007/0042010 A1 | 2/2007 | Southall et al. | |
| 2007/0196523 A1 | 8/2007 | Koganov | |
| 2008/0026974 A1 | 1/2008 | Barnhart et al. | |
| 2008/0131382 A1 | 6/2008 | Harichian et al. | |
| 2008/0260671 A1 | 10/2008 | De La Torre et al. | |
| 2008/0286217 A1 | 11/2008 | Chaudhuri | |
| 2008/0305059 A1 | 12/2008 | Chaudhuri | |
| 2008/0317887 A1 | 12/2008 | Mitchell et al. | |
| 2010/0124539 A1 | 5/2010 | Hanson | |
| 2010/0189669 A1 | 7/2010 | Hakozaki | |
| 2011/0081305 A1 | 4/2011 | Cochran et al. | |
| 2011/0081430 A1 | 4/2011 | Kaur et al. | |
| 2011/0081431 A1 | 4/2011 | Kaur et al. | |
| 2011/0171288 A1* | 7/2011 | Mohammadi et al. | 424/450 |

FOREIGN PATENT DOCUMENTS

| | | |
|---|---|---|
| DE | 101 18 894 A1 | 10/2002 |
| EP | 1 250 908 A2 | 10/2002 |
| EP | 1 974 773 A2 | 10/2008 |
| EP | 1987811 A1 | 11/2008 |
| EP | 2 045 297 A2 | 4/2009 |
| GB | 2438999 A | 12/2007 |
| JP | 2000-327557 A | 11/2000 |
| JP | 4004182 B2 | 11/2000 |
| JP | 2001 302505 A | 10/2001 |
| JP | 2004-107210 A | 4/2004 |
| JP | 2006-327965 A | 12/2006 |
| JP | 2007254412 A | 10/2007 |
| JP | 2008-184431 A | 8/2008 |
| JP | 2009084164 A | 4/2009 |
| WO | WO 03/082231 A2 | 10/2003 |
| WO | WO 2004/052330 A1 | 6/2004 |
| WO | WO 2006/097223 A1 | 9/2006 |
| WO | WO 2006/128032 A2 | 11/2006 |
| WO | WO 2008/143761 A1 | 11/2008 |

OTHER PUBLICATIONS

Fukuda et al, Inhibition by parthenolide of phorbol ester-induced transcriptional activation of inducible nitric oxide synthase gene in a human monocyte cell line THP-1, Biochemical Pharmacology, (Aug. 15, 2000) vol. 60, No. 4, pp. 595-600.*
Ochsner et al.; "Prediction of Solubility in Nonideal Multicomponent Systems Using the UNIFAC Group Contribution Model"; 1985; Journal of Pharmaceutical Sciences; 74(6): 634-637.
Xia et al.; "Dehydration of ethyl acetate-water mixtures using PVA/ceramic composite pervaporation membrane"; 2011; Separation and Purification Technology; 77: 53-59.
Hall et al.; "The Solubilization of Hexylresorcinol by an Anionic-Nonionic Surfactant Mixture"; 1966; Ameri. Jour. Pharm.; 138(6): 245-8.
Database WPI, Week 200930, Thomson Scientific, London, GB; AN 2009-H70662 XP 002635472, JP 2009 084164 A (Septem Soken KK) Apr. 23, 2009, Abstract.
Database WPI, Week 200849, Thomson Scientific, London, GB; AN 2008-H65100 XP002635473, JP 2007 254412 A (Kurarray Co Ltd) Oct. 4, 2007, Abstract.
Database WPI, Week 200223, Thomson Scientific, London, GB; AN 2002-174418 XP002635474, JP 2001 30205A (Kurarray Co Ltd) Oct. 31, 2001, Abstract.
EP Search Report for Application No. EP 10251712.5 dated May 6, 2011.

(Continued)

*Primary Examiner* — Qiuwen Mi

(57) ABSTRACT

The present invention relates to a composition comprising an NFκB-inhibitor and an anti-inflammatory compound. The anti-inflammatory compound is not an NFκB-inhibitor and has an IC50 of about 70 μg/ml or less.

4 Claims, No Drawings

OTHER PUBLICATIONS

Int'l Search Report for Application No. PCT/US2010/051080, dated Dec. 6, 2010.

V. Cenizo, et al., "LOXL as a Target to Increase the Elastin Content in Adult Skin: A Dill Extract Induces the LOXL Gene Expression," Experimental Dermatology; 2006, vol. 15(8), 574-581.

Hamamoto, et al., "Inhibitory effect of azelastine, a potent antiallergic agent, on release of tumor necrosis factor-a from activated human peripheral blood mononuclear cells and U937 cells," Exp Dermatol, 1993: 2: p. 231-235.

M. Herrmann, et al., "Blackberry Leaf Extract a New Anti-Aging Active," SOFW Journal; 2006, vol. 132(4), 42-46.

J. L Lamaison, et al., "Tannin Content and Elastase Inhibiting Activity in the Rosaceae Family," Ann. Pharmaceutiques Francaises; 1990, vol. 48, 335-340.

Y. Lin, et al., "Theaflavin-3,3'-digallate from black tea blocks the nitric oxide synthase by down-regulating the activation of NF-kB in macrophages," European Journal of Pharmacology, vol. 367, No. 2-3, Feb. 1999, p. 379-388, XP009090023.

R. Liu, et al., "Retinoic Acid Increases Elastin in Neonatal Rat Lung Fibroblast Cultures," Am. Physiol, Society, 1993, 265(5pt. 1):L430-437.

X. Liu, et al., "Elastic Fiber Homeostasis Requires Lysyl Oxidase-like 1 Protein," Nature Genetics ; 2004, vol. 36(2), 178-182.

U.S. Appl. No. 13/298,816, Johnson et al.
U.S. Appl. No. 13/362,338, Cochran et al.
U.S. Appl. No. 13/362,367, Cochran et al.

Bobin, et al. "Effects of Color Adjuvants on the Tanning Effect of Dihydroxyacetone", J. Soc. Cosmetology Chemistry, vol. 35, pp. 265-272 (1984).

* cited by examiner

COMPOSITIONS COMPRISING AN ANTI-INFLAMMATORY BLEND

CROSS REFERENCE TO RELATED APPLICATION

This application claims priority of the benefits of the filing of U.S. Provisional Application Ser. No. 61/247,992 filed on Oct. 2, 2009.

FIELD OF THE INVENTION

A composition comprising a blend of anti-inflammatory compounds is provided. The composition is useful, for example, for topical application to the skin.

BACKGROUND OF THE INVENTION

Anti-inflammatory compounds are known. The inventors have recognized that a need exists to identify new combinations of anti-inflammatory compounds that provide enhanced performance.

The inventors have found that anti-inflammatory compounds known as NFκB-inhibitors, while capable of reducing immune response via the NFκB-pathway, sometimes promote the release of the inflammatory cytokine IL-1. The inventors have also found that those anti-inflammatory compounds having a strong ability to reduce the production of cytokines by human lymphocytes stimulated with the T-cell receptor (TCR) activating agent phytohaemagglutinin, particularly those with an IC50 of about 70 µg/ml or less, are capable of reducing immune responses but sometimes have a tendency to promote the release of inflammatory cytokine IL-8.

Accordingly, it has now been discovered that combinations of an NFκB-inhibitor with an anti-inflammatory compound having a low IC50, in particular an IC50 of about 70 µg/ml or less, provide compositions that surprisingly reduce the release of both inflammatory cytokines IL-1 and IL-8 from skin and other tissues, as well generally provide desirable NFκB-inhibition in skin and other tissues.

SUMMARY OF THE INVENTION

In one aspect, the invention provides a composition comprising an NFκB-inhibitor and an anti-inflammatory compound. The anti-inflammatory compound is not an NFκB-inhibitor and has an IC50 of about 70 µg/ml or less when tested according to the ANTI-INFLAMMATORY ASSAY described herein.

According to another aspect, the invention provides a method of treating a sign of skin aging, comprising topically applying to skin in need of such treatment a composition comprising an NFκB-inhibitor and an anti-inflammatory compound. The anti-inflammatory compound is not an NFκB-inhibitor and has an IC50 of about 70 µg/ml or less when tested according to the ANTI-INFLAMMATORY ASSAY.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W). Unless stated otherwise, all ranges are inclusive of the endpoints, e.g., "from 4 to 9" includes the endpoints 4 and 9.

Products described herein may optionally be in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin or hair to treat the signs of skin aging. Such instructions may be printed on the container, label insert, or on any additional packaging.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

In certain embodiments, compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

The composition comprises an NFκB-inhibitor and an anti-inflammatory compound that is not an NFκB-inhibitor but has a low IC50. Both ingredients provide anti-inflammation benefits to the skin and other tissues, and such anti-inflammation benefits are complimentary. The inventors have surprisingly found that an anti-inflammatory compound having an IC50 of about 70 μg/ml or less combined with an NFκB inhibitor suppresses the increase in IL-1 and IL-8 cytokines that might otherwise occur from use of the individual compounds.

In one embodiment of the invention, the combination of NFκB-inhibitor and an anti-inflammatory compound having an IC50 of about 70 μg/ml or less provides reduction in the production of cytokine IL-1α of at least about 35 percent when measured by the IL-1α ASSAY set forth in Example V.

In another embodiment of the invention, the combination of NFκB-inhibitor and an anti-inflammatory compound having an IC50 of about 70 μg/ml or less provides reduction in the production of cytokine IL-8 of at least about 80 percent when measured by the IL-8 ASSAY set forth in Example VIII.

Accordingly, the invention also provides methods of reducing the production of cytokine IL-1α in skin or other tissue by at least about 35 percent as measured by the IL-1α ASSAY, by topically applying to such skin or other tissue a combination of an NFκB-inhibitor and an anti-inflammatory compound that is not an NFκB-inhibitor and has an IC50 of about 70 μg/ml or less. The combination of NFκB-inhibitor and anti-inflammatory compound may be administered to in the form of a topical composition as further described below.

Also provided are provides methods of reducing the production of cytokine IL-8 in skin or other tissue by at least about 80 percent as measured by the IL-8 ASSAY, by topically applying to such skin or other tissue a combination of an NFκB-inhibitor and an anti-inflammatory compound that is not an NFκB-inhibitor and has an IC50 of about 70 μg/ml or less. The combination of NFκB-inhibitor and anti-inflammatory compound may be administered to in the form of a topical composition as further described below.

NFκB-Inhibitor

As used herein, "NFκB-inhibitor" means a compound that inhibits the cell transcription factor nuclear kappa-B (NFκB). In one embodiment, the NFκB-inhibitor, when tested according to the NFκB-INHIBITION TEST as defined below, has a Percent NFκB Inhibition of at least about 30%, preferably at least about 50%, more preferably at least about 70%, most preferably at least about 90%, when tested at a concentration that is preferably from 1 microgram per milliliter to about 100 micrograms per milliliter. That is, the compound demonstrates the recited Percent NFκB Inhibition at at least one concentration in the range of 1 microgram per milliliter to 100 micrograms per milliliter. The compound need not provide the recited Percent NFκB Inhibition at all concentrations from 1 microgram per milliliter to 100 micrograms per milliliter, but provides the recited Percent NFκB Inhibition at least one concentration in this range.

In a preferred embodiment, the NFκB-inhibitor has a Percent NFκB Inhibition of at least about 35%, preferably at least about 55%, more preferably at least about 70%, most preferably at least about 90%, when tested at a concentration of 10 micrograms per milliliter.

The NFκB-INHIBITION TEST is conducted in the following manner. FB293 cells, a stable transfected human epithelial cell line containing the gene reporter for NF-κB are used. They may be obtained from, e.g., Panomics (Fremont, Calif.). FB293 are plated at a density of $5 \times 10^4$ cells/mL in a suitable medium, e.g., Dulbecco's modified Eagle's medium (DMEM) supplemented with 10% fetal bovine serum (Invitrogen, San Diego, Calif.). The FB293 cells are stimulated with 100 ng/mL of Tumor Necrosis Factor-α (TNFα, available from Sigma-Aldrich of St Louis, Mo.) in the presence of the test sample. Separately, a control sample is tested wherein no test sample is applied. Following a 24-hour incubation at 37° C. with 5% $CO_2$, cells are lysed with 40 μl of reporter lysis buffer (Promega, Madison, Wis.). A 20-μl aliquot of the lysate is assayed using a luciferase assay kit (Promega) and counted for 10 s in a Lmax luminometer (Molecular Devices, Sunnyvale, Calif.) with the data represented as the relative light unit/second. Percent NFκB Inhibition of the test sample is calculated as:

NFκB Inhibition=$[1-(L_{sample}/L_{control})]*100$ where $L_{sample}$ is the luminescence of the sample and $L_{control}$ is the luminescence of the control.

One or more NFκB-inhibitors may be present in the inventive composition in any suitable amount, such as from about 0.01% by weight to about 10% by weight, preferably from about 0.1% to about 20%, more preferably from about 0.1% to about 5%, even more preferably from about 0.2% to about 2%.

In one embodiment, the NFκB-inhibitor is selected from a group consisting of the following compounds: substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts of *Paulownia tomentosa* wood, and combinations thereof.

In a preferred embodiment, the NFκB-inhibitor is a substituted resorcinol. Resorcinol is a dihydroxy phenol compound (i.e., 1,3 dihydroxybenzene) having by the following structure:

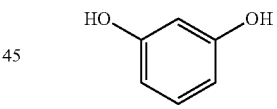

As used herein, "substituted resorcinol" means resorcinol comprising at least one substituent in the 2, 4, 5, or 6 position. Thus, the substituted resorcinol may have as few as one and as many as four substituents. Positions 1 and 3 of the substituted resorcinol comprise —OH groups, as shown above.

It is highly preferred that all of the substituents of the substituted resourcinol are free of phenyl (—$C_6H_5$ aromatic) moieties. In certain embodiments, all of the substituents are free of aromatic moieties (with or without heteroatoms).

In another embodiment, it is preferred that all of the substituents of the substituted resorcinol are free of ketone functionalities (carbonyls bonded to two other carbon atoms).

In certain preferred embodiments, all of the substituents of the substituted resorcinol are free of both phenyl functionalities and ketone functionalities.

In certain preferred embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms.

In certain other embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an akyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols include 4-hexyl resorcinol and 4-octylresorcinol, particularly 4-hexyl resorcinol. The structures of 4-hexylresorcinol and 4-octyl-resorcinol are shown below:

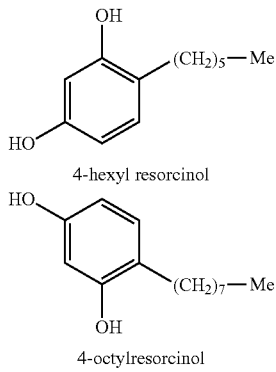

4-Hexyl resorcinol is commercially available as "SYNOVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

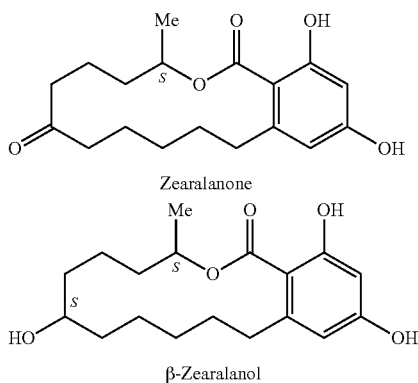

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N=O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

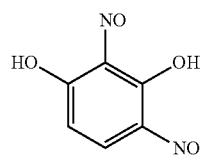

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

Paulownia is a genus of plants native to Asia which has spread gradually to Europe and the USA. In Japan, Paulownia is called kiri which refers specifically to one species, Paulownia tomentosa, also called "Princess Tree." Other names which are commonly used are "empress tree," "Foxglove Tree," "Royal Paulownia," "Pao tong" (in China) and "Odong-Namoo" (in Korea). The scientific name is "Paulownia tomentosa" with a number of synonyms reported in various literature, i.e. "Paulownia imperialis," "Paulownia recurva," and "Bignonia tomentosa." Paulownia tomentosa belongs to the family "Paulowniaceae" sometimes refered to as "Scrophulariaceae." The United States Department of Agriculture (plants.USDA.gov) Plant database identifies Princess tree by a unique symbol "PATO2," with Paulownia tomentosa and Paulownia imperialis as synonym names.

Any suitable extracts of Paulownia tomentosa wood may be used. In general, the wood of the Paulownia tomentosa tree includes wood from the stem, branches, or a combination of both. Suitable extracts of Paulownia tomentosa wood may be derived from wood chips, wood dusts and/or small cuttings, and the like.

The substituted resorcinol is present in the composition in a safe and effective amount, such as from about 0.01% to about 10%, preferably from about 0.1% to about 5%, more preferably from about 0.2% to about 2%, even more preferably from about 0.5% to about 1.5%, by weight of the composition.

Anti-Inflammatory Compound

Compositions of the present invention also include an anti-inflammatory compound that is not an NFκB-inhibitor. Specifically, the anti-inflammatory compound has a Percent NFκB Inhibition as measured by the NFκB-INHIBITION TEST that is less than about 30%, preferably less than about 20%, more preferably less than about 10%, when tested at a concentration up to about 100 micrograms per milliliter. That is, the compound demonstrates a Percent NFκB Inhibition of less than about 30%, preferably less than about 20%, more preferably less than about 10%, at all concentrations up to 100 micrograms per milliliter.

In a preferred embodiment, the anti-inflammatory compound has a Percent NFκB Inhibition of less than about 30%, preferably less than about 20%, more preferably less than about 10%, when tested at a concentration that is up to about 10 micrograms per milliliter.

The anti-inflammatory compound has an IC50 (concentration at which a compound achieves 50% inhibition of inflammation) of about 70 µg/ml or less for Interleukin-2 in the ANTI-INFLAMMATORY ASSAY set forth herein. In a preferred embodiment, the IC50 for the anti-inflammatory compound is about 50 µg/ml or less, preferably about 40 µg/ml or less, more preferably about 30 µg/ml or less.

The ANTI-INFLAMMATORY ASSAY assesses the ability of an agent to reduce the production of cytokines by human lymphocytes stimulated with the T-cell receptor (TCR) activating agent phytohaemagglutinin (PHA), and is conducted in the following manner. Human leukocytes are collected from a healthy adult male via leukopheresis, and adjusted to a density of $1\times10^6$ cells/mL in serum free lymphocyte growth medium (ExVivo-15, Biowhittaker, Walkersville, Md.). PBLs are stimulated with 10 µg/mL PHA in the presence or absence of test samples following published methods (Hamamoto Y., et al. *Exp Dermatol* 2:231-235, 1993). Following a 48-hour incubation at 37° C. with 5% $CO_2$, the supernatant is removed and evaluated for cytokine content using commercially available multiplex cytokine detection kit.

Suitable anti-inflammatory compounds having an IC50 of about 70 µg/ml or less include the following:
Phellodendron Amurense Cortex Extract (PCE)
Feverfew (*Tanacetum parthenium*)
Ginger (*Zingiber officinale*)
Ginko (*Ginko Biloba*)
Cotinus (*Cotinus coggygria*)
Goji Berry (*Lycium barbarum*)
Milk Thistle Extract (*Silybum marianum*)
Honeysuckle (*Lonicera japonica*)
Basalm of Peru (*Myroxylon pereirae*)
Sage (*Salvia officinalis*)
Cranberry Extract (*Vaccinium oxycoccos*)
Amaranth Oil (*Amaranthus cruentus*)
Pomegranate (*Punica granatum*)
Yerbe Mate (*Ilex paraguariensis* Leaf Extract)
White Lily Flower Extract (*Lilium Candidum*)
Olive Leaf Extract (*Olea europaea*)
Phloretin (apple extract)
Lifenol (Hops: *Humulus lupulus*) Extract
Licochalcone (Licorice: *Glycyrrhiza inflate* extract ingredient)
Symrelief (Bisabolol and Ginger extract).

In certain preferred embodiments, the anti-inflammatory compound is selected from: *Phellodendron amurense* cortex extract (PCE), feverfew (*Tanacetum parthenium*), ginko (*Ginko Biloba*), cotinus (*Cotinus coggygria*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract).

In certain further preferred embodiments, the anti-inflammatory compound is selected from: feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract).

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

Compositions of the present invention may include a cosmetically effective amount of one or more anti-inflammatory compounds. The compositions preferably include, on an active basis, from about 0.1% to about 10%, more preferably from about 0.5% to about 5%, of the second anti-inflammatory compound.

In the inventive composition, the weight ratio of the NFκB-inhibitor to the anti-inflammatory compound may be varied. For example, the NFκB-inhibitor and the anti-inflammatory compound may be present in a concentration by weight ratio (which is determined by dividing the concentration by weight of the NFκB-inhibitor by the concentration by weight of the anti-inflammatory compound) of about 0.001 to about 100, preferably about 0.01 to about 10, more preferably from about 0.1 to about 10.

Topical Compositions

The compositions of the present invention are applied topically to human skin or hair. In addition to the first and second anti-inflammatory compounds, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically acceptable topical carrier includes or water.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to solutions, suspensions, emulsions such as microemulsions and nanoemulsions, gels, solids and liposomes. The following are non-limiting examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin.

Examples of emollients include, but are not limited to vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Although it is preferred that the composition of the present invention includes water, the composition may alternatively be anhydrous or an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of suitable emulsifiers include those typically identified as such in the art of personal care and cosmetic formulations.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Active Agents

In one embodiment, the composition further contains another cosmetically active agent. As used herein, a "cosmetically active agent" is a compound (e.g., a synthetic compound or a compound isolated from a natural source or a natural extract) that has a cosmetic or therapeutic effect on the skin or hair, including, but not limiting to, anti-acne agents, shine control agents, anti-microbial agents, additional anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for hair and/or skin conditioning.

In one embodiment, the agent is selected from, but not limited to, the group consisting of hydroxy acids, benzoyl peroxide, D-panthenol, octyl methoxycinnimate, titanium dioxide, octyl salicylate, homosalate, avobenzone, carotenoids, amines (e.g., neutrol), retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides, amino acids such as proline, vitamins, lactobionic acid, acetyl-coenzyme A, niacin, riboflavin, thiamin, ribose, electron transporters such as NADH and FADH2, and other botanical extracts such as aloe vera, feverfew, oatmeal and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, and different forms of vitamin E like alpha, beta, gamma or delta tocopherols or their mixtures, and derivatives thereof.

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the composition, as known in the art. These include humectants, pH adjusters, chelating agents (e.g., EDTA), fragrances, and preservatives (e.g., parabens).

Water or alcohol soluble dyes may also be suitable to use in compositions of the present invention. Examples of dyes suitable for the compositions of the invention include caramel, carmine, fluorescein derivatives, methoxsalen, trioxsalen, azo dyes, anthraquinone dyes, blue azulenes, guajazulene, chamuzulene, erythrosin, bengal rose, phloxin, cyanosin, daphinin, eosin G, cosin 10B, Acid Red 51, Red Dye 4, Red Dye 40, Blue Dye 1, and Yellow Dye 5, or mixtures thereof.

When used, the amount of dye in the composition may vary from about 0.0001 to about 0.1, preferably about 0.0025 to about 0.025, weight percent based on the total weight of the composition.

The composition and formulations and products containing such compositions of the present invention may be prepared using methodology that is well known by an artisan of ordinary skill.

Methods of Use

Compositions of the present invention may be topically applied to mammalian skin that is in need of treatment for one or more signs of skin aging as described above. In one embodiment, the compositions are applied to skin in need of treatment for lines and wrinkles and/or loss of elasticity. The compositions may be applied to the skin in need of such treatment according to a suitable treatment regimen, e.g., every month, every week, every other day, every day, twice a day, or the like.

In certain embodiments, compositions of the present invention may also be useful for treating other need associated with skin. For example, compositions of the present invention may be useful for treating post-inflammatory hyperpigmentation, for reducing pore size, acne treatment, for reducing sebum production, and for scar mitigation. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mucosa or other tissue such as vaginal, oral, or ocular tissue. In certain other embodiments, compositions of the present invention are applied to mild wounds or post-surgical sites to facilitate healing, to insect bites, to poison ivy or similar skin conditions, or in general to mitigate itch. In certain other embodiments, compositions of the present invention are applied to mitigate skin irritations. The irritation may be of external origins caused by ingredients in skin care and cosmetic products such as retinoid and its derivatives, benzyol peroxide, alpha-hydroxy acids and derivatives thereof, salicylic acid, surfactants, natural plant extracts, sunscreen actives, urea, and preservatives, etc. The irritation may be of other external origins such as the sun, wind, or shaving.

The irritation may also be caused by inherent disease conditions such as acne, rosacea, atopic dermatitis, and other disease states.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example I

The NFκB-INHIBITION TEST described above was performed on test samples of Bay 11-7082 (Sigma-Aldrich, St. Louis, Mo.), Tetrahydrocurcuminoids CG (Sabinsa Corporation, Piscataway, N.J.), as well as various concentrations of 4-hexylresorcinol. The results are shown in Table 1, in which NF-κB Gene Reporter Activation (Luminescence, L) is reported for the test samples and a control sample. Percent NF-κB Inhibition is also reported.

TABLE 1

|  | NF-κB Gene Reporter Activation (Luminescence, L) | Percent NFκB Inhibition |
| --- | --- | --- |
| Untreated | 1.2 ± 0.3 | — |
| TNFα (100 ng/ml) Stimulated, "$L_{control}$" | 108.2 ± 8.5 | — |
| TNFα + 4-Hexylresorcinol (50 μg/ml) | 9.3 ± 0.9 | 91.4% |
| TNFα + 4-Hexylresorcinol (10 μg/ml) | 29.3 ± 9.2 | 72.9% |
| TNFα + 4-Hexylresorcinol (5 μg/ml) | 55.1 ± 1.7 | 50.9% |
| TNFα + 4-Hexylresorcinol (1 μg/ml) | 106.1 ± 1.9 | 1.9% |
| TNFα + Tetrahydrocurcuminoids CG (10 μg/ml) | 37.8 ± 2.6 | 65.1% |
| Bay 11-7082 (25 uM) | 11.3 ± 5.6 | 89.5% |

Bay 11-7082 and Tetrahydrocurcuminoids CG showed strong NF-κB inhibition. Unexpectedly, 4-hexylresorcinol also resulted in a substantial reduction in NFκB activation. Even more unexpectedly, 4-hexylresorcinol showed substantial NF-κB inhibition even at low concentrations.

Example II

The NFκB-INHIBITION TEST described above was performed on a series of substituted resorcinols each having a concentration of 10 μg/ml. The results are shown in Table 2.

TABLE 2

|  | Structure | Percent NF-κB Inhibition |
| --- | --- | --- |
| 4-Octylresorcinol | 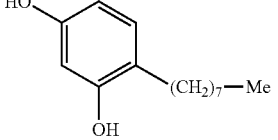 | 99.5% |
| 4-Hexylresorcinol | 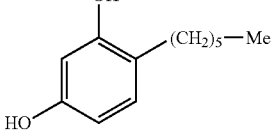 | 92.4% |

TABLE 2-continued

| Structure | | Percent NF-κB Inhibition |
|---|---|---|
| β-Zearalenol CAS#71030-11-0 | *(structure)* | 87.1% |
| β-Zearalanol CAS#42422-68-4 | *(structure)* | 76.56% |
| 2,4-Dinitrosorcinol | *(structure)* | 51.78% |
| 4-Chloroesorcinol | *(structure)* | 51.63% |
| 2,6-Dichloroesorcinol | *(structure)* | 51.54% |
| Zearalanone | *(structure)* | 50.95% |
| Phenethylresorinol | *(structure)* | 31.8% |
| 4-Dodecylresorcinol | *(structure)* | 20.87% |
| 4-Caproylresorcinol | *(structure)* | 10.25% |

TABLE 2-continued

| | Structure | Percent NF-κB Inhibition |
|---|---|---|
| C-Undecylcalix[4]-resorcinarene | 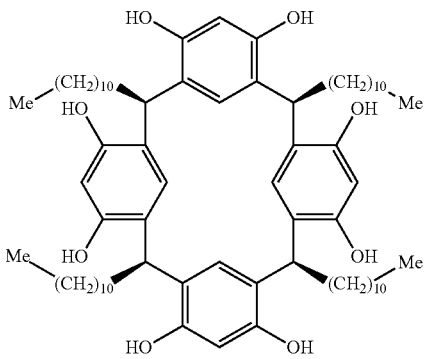 | 4.87% |
| 3-Methoxyphenol | 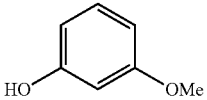 | 0% |
| 2',4'-Dihydroxypropiophenone | 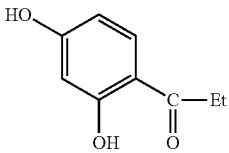 | −0.7% |
| 2,4-DIHYDROXYCINNAMIC Acid | 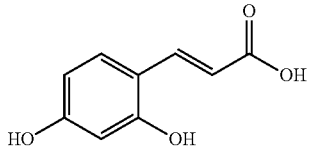 | −1.7% |
| 1,3-Dimethoxybenzene | 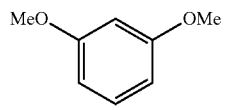 | −1.7% |

It can be seen from the data in Table 2 that superior NFκB inhibition is provided by substituted resorcinols containing only substituents free of phenyl functionalities, substituted resorcinols containing only substituents free of ketone functionalities, and substituted resorcinols comprising a substituent having 5 to 11 carbon atoms.

Example III

The NFκB-INHIBITION TEST and the ANTI-INFLAMMATORY ASSAY as described above were performed on a plurality of agents. The results are shown below in Tables 3a and 3b.

Table 3a lists anti-inflammatory compounds according to the invention having IC50 values of about 70 μg/ml or less. Table 3b lists comparative anti-inflammatory compounds having IC50 values greater than 70 μg/ml.

TABLE 3a

| Extract | NF-KB Activity (10 ug/ml) | Anti-Inflammatory Activity (IC50 ug/ml) |
|---|---|---|
| *Phellodendron Amurense* Cortex Extract (PCE) | 0% | 42.5 |
| Feverfew (*Tanacetum parthenium*) | 0% | 38.1 |
| Ginger (*Zingiber officinale*) | 6% | 61.2 |
| Ginko (*Ginko Biloba*) | 5% | 45.2 |
| Cotinus (*Cotinus coggygria*) | 0% | 44.2 |
| Goji Berry (*Lycium barbarum*) | 9.50% | 19.0 |
| Milk Thistle Extract (*Silybum marianum*) | 9.60% | 13.8 |
| Honeysuckle (*Lonicera japonica*) | 0% | 64.2 |
| Basalm of Peru (*Myroxylon pereirae*) | 3.60% | 52.9 |
| Sage (*Salvia officinalis*) | 0.68% | 56.9 |

TABLE 3a-continued

| Extract | NF-KB Activity (10 ug/ml) | Anti-Inflammatory Activity (IC50 ug/ml) |
|---|---|---|
| Cranberry Extract (*Vaccinium oxycoccos*) | 5.36% | 60.9 |
| Amaranth Oil (*Amaranthus cruentus*) | 0% | 39.8 |
| Pomegranate (*Punica granatum*) | 0.88 | 5.9 |
| Yerbe Mate (*Ilex paraguariensis* Leaf Extract) | 0.76% | 20.7 |
| White Lily Flower Extract (*Lilium Candidum*) | 0% | 32.1 |
| Olive Leaf Extract (*Olea europaea*) | 8.78% | 28.3 |
| Phloretin (apple extract) | 0% | 19.9 |
| Lifenol (Hops: *Humulus lupulus*) Extract | 0.60% | 63.7 |
| Licochalcone (Licorice: *Glycyrrhiza inflate* extract ingredient) | 0% | 54.1 |
| Symrelief (Bisabolol and Ginger extract) | 0% | 58.9 |

TABLE 3b

| Extract | NF-KB Activity (10 ug/ml) | Anti-Inflammatory Activity (IC50 ug/ml) |
|---|---|---|
| Non-Denatured Soy (*Glycine max*) | 0% | 84.1 |
| Madecassoside (*centella asiatica* extract ingredient) | 0% | 77.3 |
| Bugrane P (*Ononis spinosa*) | 0% | 71.1 |

Example IV

A composition according to the invention, Inventive Example Ex. 1 was prepared using the ingredients shown in Table 4 below.

TABLE 4

| INCI name | Trade name | Weight Percentage |
|---|---|---|
| Deionized water | Purified water | 77% |
| Pentylene glycol | HYDROLITE 5 | 5% |
| Hexyl resorcinol | SYNOVEA HR | 1% |
| Oleosome | NATRULON OSF oleosomes | 10% |
| C12-15 Alkyl Benzoate | FINSOLV TN | 4% |
| Ammonium Acryloyldimethyl-taurate/VP Copolymer | ARISTOFLEX AVC | 2% |
| *Chrysanthemum Parthenium* (Feverfew) Leaf/Flower/Stem Juice | *Tanacetum parthenium* extract | 1% |

FINSOLV TN is available from Finetex, Inc. of Elmwood Park, NJ
HYDROLITE 5 is available from Symrise of Teterboro, NJ
SYNOVEA HR is available from Sytheon of Lincoln Park, NJ
ARISTOFLEX AVC is available from Clariant of Frankfurt, Germany
NATRULON OSF oleosomes from Lonza of Allendale, NJ The composition was prepared by the following method. Synovea HR was weighed and dissolved in HYDROLITE 5 and deionized water was added to form Phase A. Oleosomes and Finsolv TN were mixed to form Phase B. Phase B was added to Phase A very slowly under continuous mixing. Mixing was continued for 15 minutes until a uniform emulsion was formed. ARISTOFLEX was added to the emulsion under continuous mixing at high speed to obtain a thick, smooth and homogenous formulation.

Example V

An IL-1α ASSAY was performed on a plurality of agents to investigate the release of the pro-inflammatory mediator, IL-1α cytokine, in human epithelial cells.

The IL-1α ASSAY was conducted as follows. KB cells were obtained from ATCC (ATCC#CCL-17, Manassas, Va.) and were plated in 96-well tissue culture treated plates at a density of 5000 cells/well in Dulbecco's modified Eagle's medium (DMEM) supplemented with 10% fetal bovine serum (Invitrogen Corp., San Diego, Calif.). After 48 hours, cells were treated with the agents described below at indicated concentrations for 24 hours, following which supernatants were collected and analyzed for IL-1α cytokine release using commercially available kits (Millipore Corp., Billerica, Mass.). The results are shown below in Table 5, below.

TABLE 5

| Example | Treatment (Dose in μg/mL) | Mean of IL-1α Release (pg/mL) |
|---|---|---|
| Comparative Example, Comp. 1 | Untreated | 0.72 |
| Comparative Example, Comp. 2 | 4-Hexylresorcinol (20 μg/mL) | 21.34 |
| Comparative Example, Comp. 3 | Tetrahydrocurcuminoids (20 μg/mL) | 2.51 |

The results suggest that NF-κB inhibitors, such as 4-hexylresorcinol and tetrahydrocurcuminoids, while capable of inhibiting NF-κB, can increase the release of cytokine IL-1α.

Example VI

Further IL-1α ASSAYS as described in Example 5 were performed. For ease of comparison, reported increases in IL-1α for 4-hexylresorcinol, phloretin, and combinations thereof were normalized to 4-hexylresorcinol (20 μg/mL, Comparative Example 2). Reported increases in IL-1α for tetrahydrocurcuminoids, feverfew, and combinations thereof were normalized to tetrahydrocurcuminoids (20 μg/mL, Comparative Example 3). The results are shown below in Table 6, below.

TABLE 6

| Example | Treatment (Dose in μg/mL) | Increase in IL-1α over untreated control (normalized) | % Reduction in IL-1α |
|---|---|---|---|
| Comparative Example, Comp. 2 | 4-Hexylresorcinol (20 μg/mL) | 100 | — |
| Comparative Example, Comp. 4 | Phloretin (10 μg/mL) | 3.82 | — |
| Comparative Example, Comp. 5 | Phloretin (50 μg/mL) | 2.39 | — |
| Comparative Example, Comp. 6 | Phloretin (100 μg/mL) | 3.34 | — |
| Inventive Example Ex. 2 | 4-Hexylresorcinol (20 μg/mL) + Phloretin (10 μg/mL) | 55.51 | 44.49% |
| Inventive Example Ex. 3 | 4-Hexylresorcinol (20 μg/mL) + Phloretin (50 μg/mL) | 10.13 | 89.87% |

TABLE 6-continued

| Example | Treatment (Dose in μg/mL) | Increase in IL-1α over untreated control (normalized) | % Reduction in IL-1α |
|---|---|---|---|
| Inventive Example Ex. 4 | 4-Hexylresorcinol (20 μg/mL) + Phloretin (100 μg/mL) | 17.01 | 82.98% |
| Comparative Example, Comp. 3 | Tetrahydrocurcuminoids (20 μg/mL) | 100 | — |
| Comparative Example, Comp. 7 | Feverfew (50 μg/mL) | 49.35 | — |
| Comparative Example, Comp. 8 | Feverfew (100 μg/mL) | 43.42 | — |
| Inventive Example Ex. 5 | Tetrahydrocurcuminoids (20 μg/mL) + Feverfew (50 μg/mL) | 42.09 | 57.91 |
| Inventive Example Ex. 6 | Tetrahydrocurcuminoids (20 μg/mL) + Feverfew (100 μg/mL) | 62.39 | 37.61 |

The results show that while NF-κB inhibitors may induce the production of cytokine IL-1α, this can be reversed by combining the NF-κB inhibitor with an anti-inflammatory compound having an IC50 of about 70 μg/ml or less (e.g., feverfew or phloretin).

Example VII

Further IL-1α ASSAYS as described in Example 5 were performed. For ease of comparison, reported increases in IL-1α were normalized to 4-hexylresorcinol (20 μg/mL, Comparative Example 2).

TABLE 7

| Example | Treatment (Dose in μg/mL) | Increase in IL-1α over untreated control (normalized) | % Reduction in IL-1α |
|---|---|---|---|
| Comparative Example, Comp. 2 | 4-Hexylresorcinol (20 μg/mL) | 100 | — |
| Comparative Example, Comp. 9 | Soy (10 μg/mL) | 2.62 | — |
| Comparative Example, Comp. 10 | Soy (50 μg/mL) | 2.59 | — |
| Comparative Example, Comp. 11 | Soy (100 μg/mL) | 4.61 | — |
| Comparative Example, Comp. 12 | 4-Hexylresorcinol (20 μg/mL) + Soy (10 μg/mL) | 81.84 | 18.16% |
| Comparative Example, Comp. 13 | 4-Hexylresorcinol (20 μg/mL) + Soy (50 μg/mL) | 65.35 | 34.65% |
| Comparative Example, Comp. 14 | 4-Hexylresorcinol (20 μg/mL) + Soy (100 μg/mL) | 82.55 | 17.45% |
| Comparative Example, Comp. 15 | Madecassoside (10 μg/mL) | 43.02 | |
| Comparative Example, Comp. 16 | Madecassoside (50 μg/mL) | 41.59 | |
| Comparative Example, Comp. 17 | Madecassoside (100 μg/mL) | 44.24 | |
| Comparative Example, Ex. 18 | 4-Hexylresorcinol (20 μg/mL) + Madecassoside (10 μg/mL) | 149.68 | −49.68% |
| Comparative Example Ex. 19 | 4-Hexylresorcinol (20 μg/mL) + Madecassoside (50 μg/mL) | 119.12 | −19.11% |
| Comparative Example Ex. 20 | 4-Hexylresorcinol (20 μg/mL) + Madecassoside (100 μg/mL) | 71.38 | 28.62% |
| Comparative Example Ex. 21 | Bugrane P (10 μg/mL) | 41.90 | |
| Comparative Example Ex. 22 | Bugrane P (50 μg/mL) | 46.73 | |
| Comparative Example Ex. 23 | Bugrane P (100 μg/mL) | 54.45 | |
| Comparative Example Ex. 24 | 4-Hexylresorcinol (20 μg/mL) + Bugrane P (10 μg/mL) | 83.04 | 16.96% |
| Comparative Example Ex. 25 | 4-Hexylresorcinol (20 μg/mL) + Bugrane P (50 μg/mL) | 89.34 | 10.66% |

These results show that combinations of NF-κB inhibitors with an anti-inflammatory compounds having an IC50 of above about 70 μg/ml may not provide as marked a reduction in the production of cytokine IL-1α as combinations of NF-κB inhibitors with an anti-inflammatory compounds having an IC50 of about 70 μg/ml or less. The above data indicates that combinations of NF-κB inhibitors with an anti-inflammatory compounds having an IC50 of above about 70 μg/ml provided less than a 35% reduction in the production of cytokine IL-1α.

It should be noted that in Comparative Examples 9-14, the soy did not dissolve in the test medium and was instead dispersed.

Example VIII

An IL-8 ASSAY was performed on a series of compositions using the method described in Example 5, except that the cytokine analyzed for was IL-8. Percent reduction in IL-8 was calculated for each sample. The results are shown in Table 8. For samples containing a combination of an NF-κB inhibitor and an anti-inflammatory compound, the percent reduction in IL-8 relative to the percent reduction in IL-8 for the corresponding dose of anti-inflammatory compound is reported.

TABLE 8

| Example | Treatment (Dose in μg/mL) | Mean of IL-8 Release (pg/mL) | Percent Reduction in IL-8 (over corresponding dose of the NON-NFkB anti-inflammatory agent) |
| --- | --- | --- | --- |
| Comparative Example Ex. 26 | Untreated | 46.05 | — |
| Comparative Example Ex. 27 | 4-Hexylresorcinol (20 μg/mL) | 14.58 | — |
| Comparative Example Ex. 28 | Feverfew (10 μg/mL) | 52.94 | — |
| Comparative Example Ex. 29 | Feverfew (50 μg/mL) | 85.48 | — |
| Comparative Example Ex. 30 | Feverfew (100 μg/mL) | 110.10 | — |
| Inventive Example Ex. 7 | 4-Hexylresorcinol (20 μg/mL) + Feverfew (10 μg/mL) | 7.11 | 85.56% |
| Inventive Example Ex. 8 | 4-Hexylresorcinol (20 μg/mL) + Feverfew (50 μg/mL) | 14.58 | 82.94% |
| Inventive Example Ex. 9 | 4-Hexylresorcinol (20 μg/mL) + Feverfew (100 μg/mL) | 8.79 | 92.02% |
| Comparative Example Ex. 31 | Phytoterra (10 μg/mL) | 157.32 | — |
| Comparative Example Ex. 32 | Phytoterra (50 μg/mL) | 211.33 | — |
| Comparative Example Ex. 33 | Phytoterra (100 μg/mL) | 183.02 | — |
| Inventive Example Ex. 10 | 4-Hexylresorcinol (20 μg/mL) + Phytoterra (10 μg/mL) | 7.36 | 95.32% |
| Inventive Example Ex. 11 | 4-Hexylresorcinol (20 μg/mL) + Phytoterra (50 μg/mL) | 8.84 | 95.82% |
| Inventive Example Ex. 12 | 4-Hexylresorcinol (20 μg/mL) + Phytoterra (100 μg/mL) | 5.25 | 97.13% |

The results show that combinations of NF-κB inhibitors and anti-inflammatory compounds having an IC50 of about 70 μg/ml or less dramatically reduced IL-8 expression, compared to the performance of either compound alone.

Example IX

Another IL-8 ASSAY as described in Example 8 was performed, except that the ratio of NF-κB inhibitor to anti-inflammatory compound having an IC50 of about 70 μg/ml or less was varied. The results are shown below in Table 9, below.

TABLE 9

| Example | Treatment (Dose in μg/mL) | Mean of IL-8 Release (pg/mL) | Percent Reduction in IL-8 (over corresponding dose of the anti-inflammatory agent) |
| --- | --- | --- | --- |
| Comparative Example Ex. 34 | Untreated | 84.46 | — |
| Comparative Example Ex. 35 | 4-Hexylresorcinol (10 μg/mL) | 73.23 | — |
| Comparative Example Ex. 36 | 4-Hexylresorcinol (20 μg/mL) | 27.05 | — |
| Comparative Example Ex. 37 | Phytoterra (2 μg/mL) | 275.31 | — |
| Comparative Example Ex. 38 | Phytoterra (20 μg/mL) | 403.49 | — |
| Comparative Example Ex. 39 | Phytoterra (100 μg/mL) | 479.59 | — |
| Inventive Example Ex. 13 | 4-Hexylresorcinol (20 μg/mL) + Phytoterra (2 μg/mL) | 18.00 | 93.46% |
| Inventive Example Ex. 14 | 4-Hexylresorcinol (20 μg/mL) + Phytoterra (20 μg/mL) | 29.16 | 92.78% |
| Inventive Example Ex. 15 | 4-Hexylresorcinol (10 μg/mL) + Phytoterra (100 μg/mL) | 36.84 | 92.32% |

These results suggest that the marked improvement in performance of the combinations of NF-κB inhibitors and anti-inflammatory compounds having an IC50 of about 70 μg/ml or less can be observed across a wide variety of weight ratios (the weight ratios were 10:1, 1:1 and 1:10 for Inventive Examples Ex. 13, 14, and 15, respectively).

Overall, the anti-inflammatory blends of the present invention provide a reduction of both inflammatory cytokines IL-1α nd IL-8, as well generally providing NFκB-inhibition.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

The invention claimed is:

1. A composition comprising:
   an NFκB-inhibitor selected from the group consisting of substituted resorcinols, (E)-3-(4-methylphenylsulfonyl)-2-propenenitrile, extracts of *Paulownia tomentosa* wood, and combinations thereof; and
   an anti-inflammatory compound that is not an NFκB-inhibitor and has an IC50 of about 70 μg/ml or less, wherein the NFκB-inhibitor and the anti-inflammatory compound are present in a weight ratio from about 1:10 to about 10:1.

2. A composition comprising:
   an NFκB-inhibitor selected from the group consisting of substituted resorcinols; and
   an anti-inflammatory compound selected from the group consisting of *Phellodendron amurense* cortex extract (PCE), feverfew (*Tanacetum parthenium*), ginkgo (*Ginkgo Biloba*), cotinus (*Cotinus coggygria*), goji berry (*Lycium barbarum*), milk thistle extract (*Silybum marianum*), amaranth oil (*Amaranthus cruentus*), pomegranate (*Punica granatum*), yerba mate (*Ilex paraguariensis* leaf extract), white lily flower extract (*Lilium Candidum*), olive leaf extract (*Olea europaea*), phloretin (apple extract), and combinations thereof, wherein the substituted resorcinol is free of phenyl moieties.

3. A composition comprising:

an NFκB-inhibitor selected from the group consisting of substituted resorcinols; and an anti-inflammatory compound selected from the group consisting of *Phellodendron amurense* cortex extract (PCE), feverfew (*Tanacetum parthenium*), ginkgo (*Ginkgo Biloba*), cotinus (*Cotinus coggygria*), goji berry (*Lycium barbarum*), milk thistle extract (*Silybum marianum*), amaranth oil (*Amaranthus cruentus*), pomegranate (*Punica granatum*), yerba mate (*Ilex paraguariensis* leaf extract), white lily flower extract (*Lilium Candidum*), olive leaf extract (*Olea europaea*), phloretin (apple extract), and combinations thereof, wherein the substituted resorcinol is 4-hexyl resorcinol.

4. A composition comprising:

an NFκB-inhibitor selected from the group consisting of substituted resorcinols; and an anti-inflammatory compound selected from the group consisting of *Phellodendron amurense* cortex extract (PCE), feverfew (*Tanacetum parthenium*), ginkgo (*Ginkgo Biloba*), cotinus (*Cotinus coggygria*), goji berry (*Lycium barbarum*), milk thistle extract (*Silybum marianum*), amaranth oil (*Amaranthus cruentus*), pomegranate (*Punica granatum*), yerba mate (*Ilex paraguariensis* leaf extract), white lily flower extract (*Lilium Candidum*), olive leaf extract (*Olea europaea*), phloretin (apple extract), and combinations thereof, wherein the NFκB-inhibitor and the anti-inflammatory compound are present in a weight ratio from about 1:10 to about 10:1.

* * * * *